(12) United States Patent
Himmelsbach et al.

(10) Patent No.: US 7,550,455 B2
(45) Date of Patent: Jun. 23, 2009

(54) 8-(PIPERAZIN-1YL)- AND 8-([1,4]DIAZEPAN-1YL)-XANTHINES, THE PREPARATION THEREOF AND THEIR USE AS PHARMACEUTICAL COMPOSITION

(75) Inventors: Frank Himmelsbach, Mittelbiberach (DE); Elke Langkopf, Warthausen (DE); Matthias Eckhardt, Biberach (DE); Mohammad Tadayyon, Ulm (DE); Leo Thomas, Biberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 444 days.

(21) Appl. No.: 10/979,468

(22) Filed: Nov. 2, 2004

(65) Prior Publication Data
US 2005/0130985 A1 Jun. 16, 2005

Related U.S. Application Data

(60) Provisional application No. 60/530,560, filed on Dec. 18, 2003.

(30) Foreign Application Priority Data
Nov. 27, 2003 (DE) .................. 103 55 304

(51) Int. Cl.
C07D 473/06 (2006.01)
C07D 519/00 (2006.01)
A61K 31/522 (2006.01)
A61P 3/10 (2006.01)
A61P 3/04 (2006.01)

(52) U.S. Cl. .................. 514/218; 514/234.2; 514/263.2; 514/263.21; 514/263.22; 514/263.34; 544/118; 544/268; 544/270; 544/272; 540/575

(58) Field of Classification Search .................. 544/118, 544/268, 270, 272; 514/218, 234.2, 263.2, 514/263.21, 263.22, 263.34; 540/575
See application file for complete search history.

(56) References Cited

U.S. PATENT DOCUMENTS

| | | | |
|---|---|---|---|
| 2,928,833 | A | 3/1960 | Leake et al. |
| 4,005,208 | A | 1/1977 | Bender |
| 4,599,338 | A | 7/1986 | Regnier et al. |
| 5,041,448 | A | 8/1991 | Janssens |
| 5,051,517 | A | 9/1991 | Findeisen |
| 5,223,499 | A | 6/1993 | Greenlee |
| 5,234,897 | A | 8/1993 | Findeisen et al. |
| 5,258,380 | A | 11/1993 | Janssens |
| 5,266,555 | A | 11/1993 | Findeisen et al. |
| 5,389,642 | A | 2/1995 | Dorsch |
| 5,470,579 | A | 11/1995 | Bonte et al. |
| 5,719,279 | A | 2/1998 | Kuefner-Muhl et al. |
| 5,753,635 | A | 5/1998 | Buckman |
| 6,303,661 | B1 | 10/2001 | Demuth |
| 6,342,601 | B1 | 1/2002 | Bantick |
| 6,548,481 | B1 | 4/2003 | Demuth et al. |
| 6,579,868 | B1 | 6/2003 | Asano |
| 6,784,195 | B2 | 8/2004 | Hale et al. |
| 6,821,978 | B2 | 11/2004 | Chackalamannil |
| 6,869,947 | B2 | 3/2005 | Kanstrup |
| 7,060,722 | B2 | 6/2006 | Kitajima |
| 7,074,794 | B2 | 7/2006 | Kitajima |
| 7,074,798 | B2 | 7/2006 | Yoshikawa |
| 7,074,923 | B2 | 7/2006 | Dahanukar |
| 7,109,192 | B2 | 9/2006 | Hauel |
| 7,179,809 | B2 | 2/2007 | Eckhardt |
| 7,183,280 | B2 | 2/2007 | Himmelsbach |
| 7,192,952 | B2 | 3/2007 | Kanstrup |
| 7,217,711 | B2 | 5/2007 | Eckhardt |
| 7,235,538 | B2 * | 6/2007 | Kanstrup et al. .............. 514/81 |
| 2002/0161001 | A1 | 10/2002 | Kanstrup |
| 2002/0169174 | A1 | 11/2002 | Chackalamannil et al. |
| 2002/0198205 | A1 | 12/2002 | Himmelsbach et al. |
| 2003/0105077 | A1 | 6/2003 | Kanstrup et al. |

(Continued)

FOREIGN PATENT DOCUMENTS

| | | |
|---|---|---|
| CA | 2136288 A1 | 5/1995 |
| CA | 2418656 A1 | 2/2002 |
| CA | 2496325 A1 | 3/2004 |
| CA | 2496249 A1 | 4/2004 |
| CA | 2505389 A1 | 5/2004 |

(Continued)

OTHER PUBLICATIONS

Busso et al., American Journal of Pathology 166:433-442 (2005).*
U.S. Appl. No. 11/744,700, filed May 4, 2007, Sieger.
U.S. Appl. No. 11/744,701, filed May 4, 2007, Kohlrausch.

(Continued)

*Primary Examiner*—Mark L Berch
(74) *Attorney, Agent, or Firm*—Michael P. Morris; Mary-Ellen M. Devlin; David L. Kershner

(57) ABSTRACT

The present invention relates to substituted xanthines of the general formula

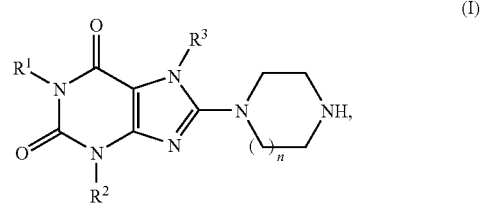

(I)

in which $R^1$ to $R^3$ and n are as defined in claims 1 to 8, their tautomers, their enantiomers, their diastereomers, their mixtures, their prodrugs and their salts, which have valuable pharmacological properties, in particular an inhibitory action on the activity of the enzyme dipeptidylpeptidase-IV (DPP-IV).

16 Claims, No Drawings

U.S. PATENT DOCUMENTS

| | | | |
|---|---|---|---|
| 2003/0199528 A1 | 10/2003 | Kanstrup | |
| 2003/0232987 A1 | 12/2003 | Dahanukar et al. | |
| 2003/0236272 A1 | 12/2003 | Carr | |
| 2004/0034014 A1 | 2/2004 | Kanstrup et al. | |
| 2004/0077645 A1 | 4/2004 | Himmelsbach et al. | |
| 2004/0082570 A1 | 4/2004 | Yoshikawa et al. | |
| 2004/0087587 A1 | 5/2004 | Himmelsbach | |
| 2004/0097510 A1 | 5/2004 | Himmelsbach et al. | |
| 2004/0116328 A1 | 6/2004 | Yoshikawa et al. | |
| 2004/0122228 A1 | 6/2004 | Maier | |
| 2004/0138214 A1* | 7/2004 | Himmelsbach et al. | .. 514/230.5 |
| 2004/0138215 A1 | 7/2004 | Eckhardt | |
| 2004/0166125 A1 | 8/2004 | Himmelsbach | |
| 2005/0020574 A1 | 1/2005 | Hauel et al. | |
| 2005/0026921 A1 | 2/2005 | Eckhardt | |
| 2005/0130985 A1 | 6/2005 | Himmelsbach | |
| 2005/0171093 A1 | 8/2005 | Eckhardt et al. | |
| 2005/0187227 A1 | 8/2005 | Himmelsbach et al. | |
| 2005/0203095 A1 | 9/2005 | Eckhardt | |
| 2005/0234108 A1 | 10/2005 | Himmelsbach et al. | |
| 2005/0261352 A1 | 11/2005 | Eckhardt | |
| 2006/0004074 A1 | 1/2006 | Eckhardt | |
| 2006/0058323 A1 | 3/2006 | Eckhardt et al. | |
| 2006/0063787 A1 | 3/2006 | Yoshikawa | |
| 2006/0079541 A1 | 4/2006 | Langkopf | |
| 2006/0094722 A1 | 5/2006 | Yasuda | |
| 2006/0100199 A1 | 5/2006 | Yoshikawa et al. | |
| 2006/0142310 A1 | 6/2006 | Pfrengle et al. | |
| 2006/0173056 A1 | 8/2006 | Kitajima | |
| 2006/0205711 A1 | 9/2006 | Himmelsbach | |
| 2006/0247226 A1 | 11/2006 | Himmelsbach | |
| 2007/0027168 A1 | 2/2007 | Pfrengle et al. | |
| 2007/0088038 A1 | 4/2007 | Eckhardt | |
| 2007/0093659 A1 | 4/2007 | Bonfanti | |
| 2007/0142383 A1 | 6/2007 | Eckhardt | |
| 2007/0185091 A1 | 8/2007 | Himmelsbach et al. | |
| 2007/0219178 A1 | 9/2007 | Muramoto | |
| 2007/0281940 A1 | 12/2007 | Dugi | |

FOREIGN PATENT DOCUMENTS

| | | |
|---|---|---|
| CA | 2508233 A1 | 6/2004 |
| CA | 2529729 A1 | 12/2004 |
| CA | 2543074 A1 | 6/2005 |
| CA | 2555050 A1 | 9/2005 |
| CA | 2556064 A1 | 9/2005 |
| CA | 2590912 A1 | 6/2006 |
| DE | 10109021 A1 | 9/2002 |
| DE | 10117803 A1 | 10/2002 |
| EP | 0149578 A2 | 7/1985 |
| EP | 0400974 A2 | 5/1990 |
| EP | 0399285 A1 | 11/1990 |
| EP | 0412358 A1 | 2/1991 |
| EP | 0524482 A1 | 1/1993 |
| EP | 0657454 A1 | 6/1995 |
| EP | 1054012 A1 | 11/2000 |
| EP | 1 338 595 A2 | 8/2003 |
| EP | 1514552 A1 | 3/2005 |
| EP | 1537880 A1 | 8/2005 |
| ES | 385302 A1 | 4/1973 |
| FR | 2707641 A1 | 1/1995 |
| JP | S37-4895 | 6/1962 |
| JP | 2003/300977 | 10/2003 |
| JP | 2006/045156 | 2/2006 |
| WO | 91/07945 A1 | 6/1991 |
| WO | 94/03456 A1 | 2/1994 |
| WO | 99/29695 A1 | 6/1999 |
| WO | WO 02/02560 A2 | 1/2002 |
| WO | 02/14271 A1 | 2/2002 |
| WO | 02/24698 A1 | 3/2002 |
| WO | WO 02/068420 A1 | 9/2002 |
| WO | WO 03/004496 A1 | 1/2003 |
| WO | WO 03/024965 A2 | 3/2003 |
| WO | 03/057200 A2 | 7/2003 |
| WO | 03/104229 A1 | 12/2003 |
| WO | 2004/018467 A2 | 3/2004 |
| WO | 2004/018468 A2 | 3/2004 |
| WO | 2004/028524 A1 | 4/2004 |
| WO | 2004/033455 A2 | 4/2004 |
| WO | WO 2004/041820 A1 | 5/2004 |
| WO | 2004/046148 A1 | 6/2004 |
| WO | 2004/048379 A1 | 6/2004 |
| WO | 2004/050658 A1 | 6/2004 |
| WO | 2004/096806 A1 | 11/2004 |
| WO | 2004/108730 A1 | 12/2004 |
| WO | 2004/111051 A1 | 12/2004 |
| WO | 2005/058901 A1 | 6/2005 |
| WO | 2005/082906 A1 | 9/2005 |
| WO | 2005/085246 A1 | 9/2005 |
| WO | 2006/029769 A1 | 3/2006 |
| WO | 2006/048427 A1 | 5/2006 |
| WO | 2006/068163 A1 | 6/2006 |
| WO | 2007/017423 A2 | 2/2007 |
| WO | WO 2008/017670 A1 | 2/2008 |

OTHER PUBLICATIONS

Augustyns, K. et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.

Beljean-Leymarie et al., Hydrazines et hydrazones hétérocycliques. IV. Synthèses de dérivés de l'hydrazine dans la série des imidazo[4,5-d]pyridazinones-4, Can. J. Chem., vol. 61, No. 11, 1983, pp. 2563-2566.

Bollag, R.J. et al; "Osteoblast-Derived Cells Express Functional Glucose-Dependent Insulinotropic Peptide Receptors," Endocrinology, vol. 141, No. 3, 2000, pp. 1228-1235.

Brittain, H.G., "Methods for the Characterization of Polymorphs: X-Ray Powder Diffraction," Polymorphism in Pharmaceutical Solids, 1999, p. 235-238.

Busso et al., "Circulating CD26 is Negatively Associated with Inflammation in Human and Experimental Arthritis," Am. J. Path., vol. 166, No. 2, Feb. 2005, pp. 433-442.

Caira, M.R., "Crystalline polymorphism of organic compounds" Topics in Current Chemistry, Springer, Berlin, vol. 198, 1998, p. 163-208.

Conarello, S.L. et al; "Mice lacking dipeptidyl peptidase IV are protected against obesity and insulin resistance," PNAS 2003; 100:6825-6830; originally published online May 14, 2003; information current as of Dec. 2006. www.pnas.org/cgi/content/full/100/11/6825.

Deacon, C.F. et al; "Dipeptidyl peptidase IV inhabitation as an approach to the treatment and prevention of type 2 diabetes: a historical perspective;" Biochemical and Biophysical Research Communications (BBRC) 294 (2002) 1-4.

DeMeester, I. et al.; "CD26, let it cut or cut it down", Review: Immunology Today; Aug. 1999, vol. 20, No. 8 pp. 367-375.

Korom, S. et al; Inhibition of CD26/dipeptidyl peptidase IV activity in vivo prolongs cardiac allograft survival in rat recipients[1,2], Transplantation, May 27, 1997, vol. 63, No. 10, pp. 1495-1500.

Pospisilik, et al; Dipeptidyl Peptidase IV Inhibitor Treatment Stimulates β-Cell Survival and Islet Neogenesis in Streptozotocin-Induced Diabetic Rats; Diabetes, vol. 52, Mar. 2003 pp. 741-750.

Rhee et al.: "Nitrogen-15-Labeled Deoxynucleosides. 3. Synthesis of [3-$^{15}$N]-2'-Deoxyadenosine" J. Am. Chem. Soc. 1990, 112, 8174-8175.

Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.

Tanaka, S.. et al; "Suppression of Arthritis by the Inhibitors of Dipeptidyl Peptidase IV," In. J. Immunopharmac., vol. 19, No. 1, pp. 15-24, 1997.

Wolff, M.E.: "Burger's Medicinal Chemistry and Drug Discovery" Fifth Edition, vol. 1: Principles and Practice, pp. 975-977, 1994, John Wiley & Sons, Inc.

Zhong, Qing et al; "Glucose-dependent insulinotropic peptide stimulates proliferation and TGF-β release from MG-63 cells," Peptides 24 (2003) 611-616.

Chemical Abstracts Accession No. 1987:95577: Abstract of Romanenko et al., "Synthesis and biological activity of 3-methyl, 7- or 8-alkyl, 7,8-dialkyl, heterocyclic, and cyclohexylaminoxanthines," Farmatsevtichnii Zhurnal, 1986, (Kiev), vol. 5, 1986, pp. 41-44.

Chemical Abstracts Accession No. 106:95577 Romanenko et al., "Synthesis and biological activity of 3-methyl, 7-or 8-alkyl-7,8-dialkyl, heterocyclic, and cyclohexylaminoxanthines," Zaporozh. Med. Institute (1986).

Yoshikawa, Seiji et al.: Chemical Abstract of Japanese Patent No. WO 2003/104229 Preparation of purinone derivatives as dipeptidylpeptidase IV (DPP-IV) inhibitors.

International Search Report for PCT/EP03/09127 mailed Nov. 28, 2003.

International Search Report for PCT/EP03/12821 mailed Mar. 30, 2004.

International Search Report for PCT/EP03/13648 mailed Apr. 5, 2004.

International Search Report for PCT/EP2007/054270 mailed Aug. 14, 2007.

International Search Report for PCT/EP2007/058181 mailed Nov. 28, 2007.

International Search Report for PCT/EP2007/054204 mailed Aug. 3, 2007.

International Search Report for PCT/EP2007/054201 mailed Aug. 29, 2007.

Patani George A. et al.: "Bioisoterism : A Rational Approach in Drug Design", Chemical Reviews, 1996, vol. 96, No. 8, pp. 3147-3176.

Zejc, Alfred et al; Badania Nad Piperazynowymi Pochodnymi Dwumetyloksantyn; Acta Polon. Pharm. XXXV. Nr 4, 1976, pp. 417-421.

Januvia; Patient Information; Oct. 2007.

Cygankiewicz, Andrzej et al., Investigations into the Piperazine Derivatives of Dimethylxanthine:, Acta Polon. Pharm. [Papers of Polish Pharmacology], XXXOV, No. 5, pp. 607-612, 1977.

* cited by examiner

8-(PIPERAZIN-1YL)- AND 8-([1,4]DIAZEPAN-1YL)-XANTHINES, THE PREPARATION THEREOF AND THEIR USE AS PHARMACEUTICAL COMPOSITION

RELATED APPLICATIONS

Benefit of U.S. Provisional Application Ser. No. 60/530,560, filed on Dec. 18, 2003, is hereby claimed, and which application is incorporated herein in its entirety.

FIELD OF THE INVENTION

The present invention relates to novel substituted xanthines of the general formula

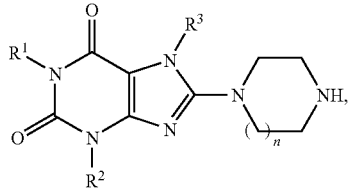

their tautomers, their enantiomers, their diastereomers, their mixtures, their prodrugs and their salts, in particular their physiologically tolerable salts with inorganic or organic acids, which have valuable pharmacological properties, in particular an inhibitory action on the activity of the enzyme dipeptidylpeptidase-IV (DPP-IV), their preparation, their use for the prevention or treatment of illnesses or conditions which are connected with increased DPP-IV activity or can be prevented or alleviated by reduction of the DPP-IV activity, in particular of diabetes mellitus type I or type II, the medicaments comprising a compound of the general formula (I) or a physiologically tolerable salt thereof, and processes for their preparation.

Xanthines having a DPP-IV-inhibiting action are already known from WO 02/02560, WO 03/004496, WO 03/024965, EP 1 338 595 and WO 02/68420. These, however, differ markedly structurally from the compound according to the invention, in particular with respect to the substituents in position 7 and/or 8, or with respect to the group in the 1-position and the combination of groups in position 1 and 8.

In the above formula 1

$R^1$ is a heteroaryl-$C_{1-3}$-alkyl group, where the term heteroaryl is to be understood as meaning a phenylpyrimidinyl, quinolinyl, isoquinolinyl, quinazolinyl, quinoxalinyl, naphthyridinyl or phenanthridinyl group and the abovementioned heteroaryl groups are substituted by $R^{10}$, $R^{11}$ and $R^{12}$, where $R^{10}$ is a hydrogen atom, a fluorine, chlorine or bromine atom or a methyl, difluoromethyl, trifluoromethyl, phenyl, cyano, methoxy, difluoromethoxy, trifluoromethoxy, amino, methylamino, dimethylamino, pyrrolidin-1-yl, piperidin-1-yl or morpholin-4-yl group, $R^{11}$ is a hydrogen atom or a methyl, methoxy or cyano group and $R^{12}$ is a hydrogen atom or a methyl group, or a naphthyl-$C_{1-3}$-alkyl group, in which the naphthyl moiety is substituted by $R^{13}$ and $R^{14}$, where $R^{13}$ is a hydrogen atom, a fluorine, chlorine or bromine atom or a methyl, difluoromethyl, trifluoromethyl, cyano, methoxy, difluoromethoxy or trifluoromethoxy group and $R^{14}$ is a hydrogen atom or a methyl, methoxy or cyano group, $R^2$ is a methyl, ethyl, propyl, isopropyl, cyclopropyl or phenyl group, $R^3$ is a 2-butyn-1-yl group or a 1-buten-1-yl, 2-buten-1-yl or 3-methyl-2-buten-1-yl group, and n is the number 1 or 2, their tautomers, their enantiomers, their diastereomers, their mixtures, their prodrugs and their salts.

Prodrugs are understood as meaning derivatives which are converted in vivo into the actually active compound. In the compounds according to the invention, the NH group of the piperazino or -[1,4]diazepan-1-yl group can in particular be substituted by a group which is cleavable in vivo. Groups of this type are described, for example, in WO 98/46576 and by N. M. Nielsen et al. in International Journal of Pharmaceutics 39, 75-85 (1987).

A group which can be cleaved in vivo by an imino or amino group is to be understood as meaning, for example, a hydroxyl group, an acyl group such as a phenylcarbonyl group optionally mono- or disubstituted by fluorine, chlorine, bromine or iodine atoms, by $C_{1-3}$-alkyl groups or $C_{1-3}$-alkyloxy groups, where the substituents can be identical or different, a pyridinoyl group or a $C_{1-16}$-alkanoyl group such as the formyl, acetyl, propionyl, butanoyl, pentanoyl or hexanoyl group, a 3,3,3-trichlorpropionyl or allyloxycarbonyl group, a $C_{1-16}$-alkyloxycarbonyl or $C_{1-16}$-alkylcarbonyloxy group, in which hydrogen atoms can be completely or partly replaced by fluorine or chlorine atoms, such as the methoxycarbonyl, ethoxycarbonyl, propoxycarbonyl, isopropoxycarbonyl, butoxycarbonyl, tert-butoxycarbonyl, pentoxycarbonyl, hexoxycarbonyl, octyloxycarbonyl, nonyloxycarbonyl, decyloxycarbonyl, undecyloxycarbonyl, dodecyloxycarbonyl, hexadecyloxycarbonyl, methylcarbonyloxy, ethylcarbonyloxy, 2,2,2-trichloroethylcarbonyloxy, propylcarbonyloxy, isopropylcarbonyloxy, butylcarbonyloxy, tert-butylcarbonyloxy, pentylcarbonyloxy, hexylcarbonyloxy, octylcarbonyloxy, nonylcarbonyloxy, decylcarbonyloxy, undecylcarbonyloxy, dodecylcarbonyloxy or hexadecylcarbonyloxy group, a phenyl-$C_{1-6}$-alkyloxycarbonyl group such as the benzyloxycarbonyl, phenylethoxycarbonyl or phenylpropoxycarbonyl group, a 3-aminopropionyl group, in which the amino group can be mono- or disubstituted by $C_{1-6}$-alkyl or $C_{3-7}$-cycloalkyl groups and the substituents can be identical or different, a $C_{1-3}$-alkylsulfonyl-$C_{2-4}$-alkyloxycarbonyl, $C_{1-3}$-alkyloxy-$C_{2-4}$-alkyloxy-$C_{2-4}$-alkyloxycarbonyl, $R_p$—CO—O—($R_qCR_r$)—O—CO, $C_{1-6}$-alkyl-CO—NH—($R_sCR_t$)—O—CO or $C_{1-6}$-alkyl-CO—O—($R_sCR_t$)—($R_sCR_t$)—O—CO group, in which $R_p$ is a $C_{1-8}$-alkyl, $C_{5-7}$-cycloalkyl, $C_{1-8}$-alkyloxy, $C_{5-7}$-cycloalkyloxy, phenyl or phenyl-$C_{1-3}$-alkyl group, $R_q$ is a hydrogen atom, a $C_{1-3}$-alkyl, $C_{5-7}$-cycloalkyl or phenyl group, $R_r$ is a hydrogen atom or a $C_{1-3}$-alkyl group and $R_s$ and $R_t$, which can be identical or different, are hydrogen atoms or $C_{1-3}$-alkyl groups.

Preferred compounds of the general formula I are those in which $R^1$ is a heteroarylmethyl group, where the term heteroaryl is to be understood as meaning a phenylpyrimidinyl, quinolinyl, isoquinolinyl, quinazolinyl, quinoxalinyl, naphthyridinyl or phenanthridinyl group and the abovementioned heteroaryl groups are substituted by $R^{10}$, $R^{11}$ and $R^{12}$, where $R^{10}$ is a hydrogen atom or a methyl, difluoromethyl, trifluoromethyl, phenyl, cyano, methoxy, difluoromethoxy, trifluoromethoxy, amino, methylamino, dimethylamino, pyrrolidin-1-yl, piperidin-1-yl or morpholin-4-yl group, $R^{11}$ is a hydrogen atom or a methyl or cyano group and $R^{12}$ is a hydrogen atom or a methyl group, or a naphthylmethyl group, in which the naphthyl moiety is substituted by $R^{13}$ and $R^{14}$, where $R^{13}$ is a hydrogen atom, a fluorine, chlorine or bromine atom or a methyl, difluoromethyl, trifluoromethyl, cyano, methoxy, difluoromethoxy or trifluoromethoxy group and $R^{14}$ is a hydrogen atom or a methyl or cyano group, $R^2$ is a methyl, ethyl, propyl, isopropyl, cyclopropyl or phenyl group, $R^3$ is a 2-butyn-1-yl group or a 1-buten-1-yl, 2-buten-1-yl or 3-methyl-2-buten-1-yl group, and n is the number 1 or 2, their tautomers, their mixtures and their salts.

Particularly preferred compounds of the general formula I are those in which $R^1$ is a heteroarylmethyl group, where the term heteroaryl is to be understood as meaning a phenylpyrimidinyl, quinolinyl, isoquinolinyl, quinazolinyl, quinoxalinyl, naphthyridinyl or phenanthridinyl group and the abovementioned heteroaryl groups are substituted by R-hu 10, $R^{11}$ and $R^{12}$, where $R^{10}$ is a hydrogen atom or a methyl, phenyl, cyano, methoxy, amino, methylamino, dimethylamino, pyrrolidin-1-yl, piperidin-1-yl or morpholin-4-yl group, $R^{11}$ is a hydrogen atom or a methyl or cyano group and $R^{12}$ is a hydrogen atom or a methyl group, or a naphthylmethyl group, in which the naphthyl moiety is substituted by $R^{13}$ and $R^{14}$, where $R^{13}$ is a hydrogen atom, a fluorine atom or a methyl, cyano or methoxy group and $R^{14}$ is a hydrogen atom or a methyl or cyano group, $R^2$ is a methyl group, $R^3$ is a 2-butyn-1-yl group and n is the number 1 or 2, their tautomers, their mixtures and their salts.

Very particularly preferred compounds are those in which $R^1$ is a methyl group, which is substituted by a fluoronaphthyl, methoxynaphthyl, cyanonaphthyl, dicyanonaphthyl, phenylpyrimidinyl, quinolinyl, fluoroquinolinyl, methylquinolinyl, cyanoquinolinyl, isoquinolinyl, methylisoquinolinyl, cyanoisoquinolinyl, quinazolinyl, methylquinazolinyl, phenylquinazolinyl, (dimethylamino)-quinazolinyl, (morpholin-4-yl)quinazolinyl, quinoxalinyl, methylquinoxalinyl, dimethylquinoxalinyl, trimethylquinoxalinyl, phenylquinoxalinyl or naphthyridinyl group, $R^2$ is a methyl group, $R^3$ is a 2-butyn-1-yl group, and n is the number 1 or 2, their tautomers, their mixtures and their salts;

in particular, those compounds are preferred in which $R^1$ is a methyl group, which is substituted by a cyanoquinolinyl, methylisoquinolinyl, cyanoisoquinolinyl, quinazolinyl, methylquinazolinyl, phenylquinazolinyl, dimethylquinoxalinyl or naphthyridinyl group, $R^2$ is a methyl group, $R^3$ is a 2-butyn-1-yl group and n is the number 1 or 2, their tautomers and their salts.

Those compounds of the general formula I form a preferred subgroup in which $R^1$, $R^2$ and $R^3$ are defined as mentioned above and n is the number 1, their tautomers and their salts.

Those compounds of the general formula I form a second subgroup in which $R^1$, $R^2$ and $R^3$ are defined as mentioned above and n is the number 2, their tautomers and their salts.

In particular, the following compounds may be mentioned:

(a) 1-[(4-Methylquinazolin-2-yl)methyl]-3-methyl-7-(2-butyn-1-yl)-8-(piperazin-1-yl)-xanthine (b) 1-[(4-Phenylquinazolin-2-yl)methyl]-3-methyl-7-(2-butyn-1-yl)-8-(piperazin-1-yl)-xanthine (c) 1-[([1,5]-Naphthyridin-2-yl)methyl]-3-methyl-7-(2-butyn-1-yl)-8-(piperazin-1-yl)-xanthine and their tautomers and their salts.

According to the invention, the compounds of the general formula I are obtained by processes known per se, for example by the following processes:

a) Reaction of a Compound of the Formula

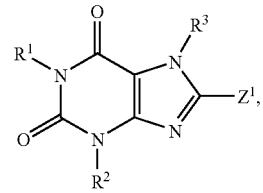

(II)

in which $R^1$ to $R^3$ are defined as mentioned at the outset and $Z^1$ is a leaving group such as a halogen atom, a substituted hydroxyl, mercapto, sulphinyl, sulphonyl or sulphonyloxy group such as a chlorine or bromine atom, a methanesulfonyl or methanesulfonyloxy group, with piperazine or [1,4]diazepane or their salts.

The reaction is expediently carried out in a solvent such as isopropanol, butanol, tetrahydrofuran, dioxane, dimethylformamide, dimethyl sulphoxide, ethylene glycol monomethyl ether, ethylene glycol diethyl ether or sulpholane optionally in the presence of an inorganic or tertiary organic base, e.g. sodium carbonate, potassium carbonate or potassium hydroxide, a tertiary organic base, e.g. triethylamine, or in the presence of N-ethyldiisopropylamine (Hünig's base), where these organic bases can simultaneously also serve as solvents, and optionally in the presence of a reaction accelerator such as an alkali metal halide or a catalyst based on palladium at temperatures between −20 and 180° C., but preferably at temperatures between −10 and 120° C. The reaction, however, can also be carried out without solvent or in an excess of piperazine or [1,4]diazepane.

b) Deprotection of a Compound of the Formula

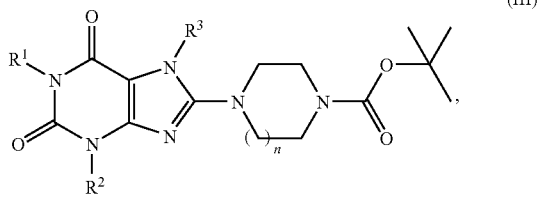

(III)

in which $R^1$, $R^2$ and $R^3$ are defined as mentioned at the outset.

The cleavage of the tert-butyloxycarbonyl group is preferably carried out by treatment with an acid such as trifluoroacetic acid or hydrochloric acid or by treatment with bromotrimethylsilane or iodotrimethylsilane optionally using a solvent such as methylene chloride, ethyl acetate, dioxane, methanol, isopropanol or diethyl ether at temperatures between 0 and 80° C.

In the reactions described above, reactive groups optionally present such as amino, alkylamino or imino groups can be protected during the reaction by customary protective groups, which are cleaved again after the reaction.

For example, possible protective groups for an amino, alkylamino or imino group are the formyl, acetyl, trifluoroacetyl, ethoxycarbonyl, tert-butoxycarbonyl, benzyloxycarbonyl, benzyl, methoxybenzyl or 2,4-dimethoxybenzyl group and for the amino group additionally the phthalyl group.

The optionally subsequent cleavage of a used protective group is carried out, for example, hydrolytically in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C.

The cleavage of a benzyl, methoxybenzyl or benzyloxycarbonyl group, however, is carried out, for example, hydrogenolytically, e.g. using hydrogen in the presence of a catalyst such as palladium/carbon in a suitable solvent such as methanol, ethanol, ethyl acetate or glacial acetic acid optionally with addition of an acid such as hydrochloric acid at temperatures between 0 and 100° C., but preferably at room temperatures between 20 and 60° C., and at a hydrogen pressure of 1 to 7 bar, but preferably of 3 to 5 bar. The cleavage of a 2,4-dimethoxybenzyl group, however, is preferably carried out in trifluoroacetic acid in the presence of anisole.

The cleavage of a tert-butyl or tert-butyloxycarbonyl group is preferably carried out by treatment with an acid such as trifluoroacetic acid or hydrochloric acid or by treatment with iodotrimethylsilane optionally using a solvent such as methylene chloride, dioxane, methanol or diethyl ether.

The cleavage of a trifluoroacetyl group is preferably carried out by treatment with an acid such as hydrochloric acid optionally in the presence of a solvent such as acetic acid at temperatures between 50 and 120° C. or by treatment with sodium hydroxide solution optionally in the presence of a solvent such as tetrahydrofuran at temperatures between 0 and 50° C.

The cleavage of a phthalyl group is preferably carried out in the presence of hydrazine or a primary amine such as methylamine, ethylamine or n-butylamine in a solvent such as methanol, ethanol, isopropanol, toluene/water or dioxane at temperatures between 20 and 50° C.

Furthermore, the compounds of the general formula I obtained can be separated, as has been already mentioned at the outset, into their enantiomers and/or diastereomers. For example, cis/trans mixtures can thus be separated into their cis and trans isomers, and compounds having at least one optically active carbon atom can be separated into their enantiomers.

For example, the cis/trans mixtures thus obtained can be separated by chromatography into their cis and trans isomers, the compounds of the general formula I obtained, which occur as racemates, can be separated by methods known per se (see Allinger N. L. and Eliel E. L. in "Topics in Stereochemistry", Vol. 6, Wiley Interscience, 1971) into their optical antipodes and compounds of the general formula I having at least 2 asymmetric carbon atoms can be separated on the basis of their physicochemical differences according to methods known per se, e.g. by chromatography and/or fractional crystallization, into their diastereomers, which, if they are obtained in racemic form, can then be separated into the enantiomers as mentioned above.

The separation of enantiomers is preferably carried out by column separation on chiral phases or by recrystallizing from an optically active solvent or by reacting with an optically active substance, in particular acids and their activated derivatives or alcohols, forming salts or derivatives such as, for example, esters or amides, with the racemic compound and separating the diastereomeric salt mixture or derivative obtained in this way, e.g. on the basis of different solubilities, it being possible to liberate the free antipodes from the pure diastereomeric salts or derivatives by the action of suitable agents. Particularly common, optically active acids are, for example, the D and L forms of tartaric acid or dibenzoyltartaric acid, di-O-p-toluoyl-tartaric acid, malic acid, mandelic acid, camphorsulphonic acid, glutamic acid, aspartic acid or quinic acid. A possible optically active alcohol is, for example, (+)- or (−)-menthol and an optically active acyl group in amides is, for example, (+)- or (−)-menthyloxycarbonyl.

In addition, the compounds of the formula I obtained can be converted into their salts, in particular for pharmaceutical administration into their physiologically tolerable salts with inorganic or organic acids. Possible acids for this are, for example, hydrochloric acid, hydrobromic acid, sulphuric acid, methanesulphonic acid, phosphoric acid, fumaric acid, succinic acid, lactic acid, citric acid, tartaric acid or maleic acid.

The compounds of the general formulae II and III used as starting substances are either known from the literature or they are obtained by processes known per se from the literature (see Examples I to IV).

As already mentioned at the outset, the compounds of the general formula I according to the invention and their physiologically tolerable salts have valuable pharmacological properties, in particular an inhibitory action on the enzyme DPP-IV.

The biological properties of the novel compounds were tested as follows:

The ability of the substances and their corresponding salts to inhibit DPP-IV activity can be shown in a test set-up in which an extract of the human colon carcinoma cell line Caco-2 is utilized as the DPP-IV source. The differentiation of the cells, in order to induce the DPP-IV expression, was carried out according to the description of Reiher et al. in an article having the title "Increased expression of intestinal cell line Caco-2", which appeared in Proc. Natl. Acad. Sci. Vol.

90, pages 5757-5761 (1993),. The cell extract was obtained from the cells solubilized in a buffer (10 mM tris HCl, 0.15 M NaCl, 0.04 t.i.u. aprotinin, 0.5% Nonidet-P40, pH 8.0) by centrifugation at 35000 g for 30 minutes at 4° C. (for the removal of cell debris).

The DPP-IV assay was carried out as follows:

50 μl of substrate solution (AFC; AFC is amido-4-trifluoromethylcoumarin), final concentration 100 μM, were introduced into black microtitre plates. 20 μl of assay buffer (final concentrations 50 mM tris HCl pH 7.8, 50 mM NaCl, 1% DMSO) were pipetted in. The reaction was started by addition of 30 μl of solubilized Caco-2 protein (final concentration 0.14 μg of protein per well). The test substances to be investigated were typically added prediluted in 20 μl, the assay buffer volumes then being correspondingly reduced. The reaction was carried out at room temperature; the incubation period was 60 minutes. The fluorescence was then measured in a Victor 1420 multilabel counter, the excitation wavelength being at 405 nm and the emission wavelength at 535 nm. Blank values (corresponding to 0% activity) were obtained in batches without Caco-2 protein (volumes replaced by assay buffer), control values (corresponding to 100% activity) were obtained in batches without addition of substance. The potencies of the respective test substances, expressed as $IC_{50}$ values, were calculated from dose-response curves, which consisted of 11 measurement points in each case. The following results were obtained thereby:

| Compound (Example No.) | DPP IV inhibition $IC_{50}$ [nM] |
|---|---|
| 1 | 3 |
| 1(1) | 17 |
| 1(2) | 9 |
| 1(3) | 6 |

The compounds prepared according to the invention are highly tolerable, since, for example, after oral administration of 10 mg/kg of the compound of Example 1 to rats in was not possible to observe any changes in the behaviour of the animals.

With respect to the ability to inhibit the DPP-IV activity, the compounds of the general formula I according to the invention and their corresponding pharmaceutically acceptable salts are suitable for influencing all those conditions or illnesses which can be influenced by an inhibition of the DPP-IV activity. It is therefore to be expected that the compounds according to the invention are suitable for the prevention of illnesses or conditions such as diabetes mellitus type 1 and type 2, prediabetes, reduction of the glucose tolerance or changes in the fasting blood sugar, diabetic complications (such as, for example, retinopathy, nephropathy or neuropathies), metabolic acidosis or ketosis, reactive hypoglycaemia, insulin resistance, metabolic syndrome, dyslipidaemias of all sorts of origin, arthritis, atherosclerosis and related diseases, adiposity, allograft transplantation and osteoporosis caused by calcitonin. Moreover, these substances are suitable for preventing B cell degeneration such as, for example, apoptosis or necrosis of pancreatic B cells. The substances are further suitable for improving or restoring the functionality of pancreatic cells, in addition for increasing the number and size of pancreatic B cells. Additionally and justified by the role of the glucagon-like peptides, such as, for example, GLP-1 and GLP-2 and their link with DPP-IV Inhibition, it is expected that the compounds according to the invention are suitable, inter alia, for achieving a sedating or anxiolytic effect, moreover of favourably influencing catabolic conditions after operations or hormonal stress responses or of being able to reduce the mortality and morbidity after myocardial infarct. Moreover, they are suitable for the treatment of all conditions which are connected with the abovementioned effects and are mediated by GLP-1 or GLP-2. The compounds according to the invention can likewise be employed as diuretics or antihypertensives and are suitable for the prevention and treatment of acute kidney failure. Furthermore, the compounds according to the invention can be employed for the treatment of inflammatory diseases of the airways. Likewise, they are suitable for the prevention and therapy of chronic inflammatory bowel diseases such as, for example, irritable bowel syndrome (IBS), Crohn's disease or ulcerative colitis as well as in pancreatitis. In addition, it is expected that they can be employed in any type of injury or disturbance in the gastrointestinal tract and, for example, in cases of colitis and enteritis. Moreover, it is expected that DPP-IV inhibitors and thus also the compounds according to the invention can be used for the treatment of infertility or for the improvement of fertility in man or in the mammalian body, in particular if the infertility is connected with insulin resistance or with polycystic ovarian syndrome. On the other hand, these substances are suitable for influencing the motility of the sperm and and can thus be employed as contraceptives for use in man. Moreover, the substances are suitable for influencing growth hormone deficiency states, which are accompanied by low growth, and can be usefully employed in all indications in which growth hormone can be used. On account of their inhibitory action against DPP IV, the compounds according to the invention are also suitable for the treatment of various autoimmune diseases such as, for example, rheumatoid arthritis, multiple sclerosis, cases of thyroiditis and Basedow's disease etc. Moreover, they can be employed in viral diseases and, for example, in HIV infections, for the stimulation of haematopoiesis, in benign prostate hyperplasia, in cases of gingivitis, and for the treatment of neuronal defects and neurodegenerative diseases such as, for example, Alzheimer's disease. Compounds described are likewise to be used for the therapy of tumours, in particular for modifying tumour invasion and formation of metastases; examples here are use in T cell lymphomas, acute lymphoblastic leukaemia, cell-based thyroid carcinomas, basal cell carcinomas or breast carcinomas. Further indications are stroke, cases of ischaemia of all sorts of origin, Parkinson's disease and migraine. Moreover, further indication areas are cases of follicular and epidermal hyperkeratosis, increased keratinocyte proliferation, psoriasis, cases of encephalomyelitis, cases of glomerulonephritis, cases of lipodystrophy, and psychosomatic, depressive and neuropsychiatric diseases of all sorts of origin.

The compounds according to the invention can also be used in combination with other active compounds. The therapeutics suitable for such a combination include, for example, antidiabetics, such as, for example, metformin, sulphonylureas (e.g. glibenclamide, tolbutamide, glimepiride), nateglinide, repaglinide, thiazolidinediones (e.g. rosiglitazone, pioglitazone), PPAR gamma agonists (e.g. GI 262570) and antagonists, PPAR gamma/alpha modulators (e.g. KRP 297), PPAR gamma/alpha/delta modulators, AMPK activators, ACC1 and ACC2 inhibitors, DGAT inhibitors, SMT3 receptor agonists, 11β-HSD inhibitors, FGF19 agonists or mimetics, alpha-glucosidase inhibitors (e.g. acarbose, voglibose), other DPPIV inhibitors, alpha2 antagonists, insulin and insulin analogues, GLP-1 and GLP-1 analogues (e.g. exendin-4)

or amylin. In addition, SGLT2 inhibitors such as T-1095 or KGT-1251 (869682), inhibitors of protein tyrosine phosphatase 1, substances which influence deregulated glucose production in the liver, such as, for example, inhibitors of glucose 6-phosphatase, or of fructose 1,6-bisphosphatase, of glycogen phosphorylase, glucagon receptor antagonists and inhibitors of phosphoenol pyruvate carboxykinase, of glycogen synthase kinase or of pyruvate dehydrokinase, hypolipidaemics, such as, for example, HMG-CoA reductase inhibitors (e.g. simvastatin, atorvastatin), fibrates (e.g. bezafibrate, fenofibrate), nicotinic acid and its derivatives, PPAR alpha agonists, PPAR delta agonists, ACAT inhibitors (e.g. avasimibe) or cholesterol absorption inhibitors such as, for example, ezetimibe, bile acid-binding substances such as, for example, colestyramine, inhibitors of ileal bile acid transport, HDL-increasing compounds such as, for example, inhibitors of CETP or regulators of ABC1 or LXRalpha antagonists, LXRbeta agonists or LXRalpha/beta regulators or active compounds for the treatment of obesity, such as, for example, sibutramine or tetrahydrolipstatin, dexfenfluramine, axokine, antagonists of the cannbinoid1 receptor, MCH-1 receptor antagonists, MC4 receptor agonists, NPY5 or NPY2 antagonists or $\beta_3$-agonists such as SB-418790 or AD-9677 as well as agonists of the 5HT2c receptor.

In addition, a combination with medicaments for influencing high blood pressure such as, for example, AII antagonists or ACE inhibitors, diuretics, β-blockers, Ca antagonists and others or combinations thereof is suitable.

The dose necessary to achieve an appropriate action is expediently, in the case of intravenous administration, 1 to 100 mg, preferably 1 to 30 mg, and in the case of oral administration 1 to 1000 mg, preferably 1 to 100 mg, in each case 1 to 4× daily. For this purpose, the compounds of the formula I prepared according to the invention, if appropriate in combination with other active substances, can be incorporated together with one or more inert customary vehicles and/or diluents, e.g. maize starch, lactose, sucrose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fat-containing substances such as hard fat or their suitable mixtures, in customary galenical preparations such as tablets, coated tablets, capsules, powders, suspensions or suppositories.

The following examples are intended to illustrate the invention in greater detail:

Preparation of the starting compounds:

EXAMPLE I

1-[(4-Methylquinazolin-2-yl)methyl]-3-methyl-7-(2-butyn-1-yl)-8-bromoxanthine

A mixture of 28.91 g of 3-methyl-7-(2-butyn-1-yl)-8-bromoxanthine, 20.00 g of 2-chloromethyl-4-methylquinazoline and 27.74 g of potassium carbonate in 235 ml of N-methylpyrrolidone is warmed to 75° C. and stirred at this temperature for six hours. Subsequently, the reaction mixture is slowly treated with 235 ml of water, a pale precipitate depositing. The suspension is cooled in an ice bath. The precipitate is filtered off with suction, washed with water and a little petroleum ether and dried at 50° C. in a circulating air drying oven.

Yield: 40.8 g (93% of theory) Mass spectrum (ESI$^+$): m/z=453, 455 [M+H]$^+$

The following compounds are obtained analogously to Example I:

(1) 1-[(3-Methylisoquinolin-1-yl)methyl]-3-methyl-7-(2-butyn-1-yl)-8-bromoxanthine $R_f$: 0.40 (silica gel, ethyl acetate/petroleum ether=1:1) Mass spectrum (ESI$^+$): m/z=452, 454 [M+H]$^+$ (2) 1-[(Phenanthridin-6-yl)methyl]-3-methyl-7-(2-butyn-1-yl)-8-bromoxanthine $R_f$: 0.50 (silica gel, cyclohexane/ethyl acetate=3:1) Mass spectrum (ESI$^+$): m/z=488, 490 [M+H]$^+$ (3) 1-[(4-Phenylquinazolin-2-yl)methyl]-3-methyl-7-(2-butyn-1-yl)-8-bromoxanthine (carrying out in N,N-dimethylformamide at 80° C.)

$R_f$: 0.83 (silica gel, ethyl acetate/petroleum ether=4:1) Mass spectrum (ESI$^+$): m/z=515, 517 [M+H]$^+$ (4) 1-[(2,3-Dimethylquinoxalin-6-yl)methyl]-3-methyl-7-(2-butyn-1-yl)-8-bromoxanthine (carrying out in N,N-dimethylformamide at 80° C.)

$R_f$: 0.50 (silica gel, ethyl acetate/petroleum ether=4:1) Mass spectrum (ESI$^+$): m/z=467, 469 [M+H]$^+$ (5) 1-[(4-Cyanoisoquinolin-1-yl)methyl]-3-methyl-7-(2-butyn-1-yl)-8-bromoxanthine (carrying out in N,N-dimethylformamide at 80° C.)

$R_f$: 0.80 (silica gel, ethyl acetate/petroleum ether=4:1) Mass spectrum (ESI$^+$): m/z=463, 465 [M+H]$^+$ (6) 1-[(1-Cyanoisoquinolin-3-yl)methyl]-3-methyl-7-(2-butyn-1-yl)-8-bromoxanthine (carrying out in N,N-dimethylformamide at 80° C.)

$R_f$: 0.75 (silica gel, ethyl acetate/petroleum ether=4:1) Mass spectrum (ESI$^+$): m/z=463, 465 [M+H]$^+$ (7) 1-[([1,5]-Naphthyridin-2-yl)methyl]-3-methyl-7-(2-butyn-1-yl)-8-bromoxanthine (carrying out in N,N-dimethylformamide at 80° C.)

$R_f$: 0.39 (silica gel, ethyl acetate) Mass spectrum (ESI$^+$): m/z=439, 441 [M+H]$^+$

EXAMPLE II

3-Methyl-7-(2-butyn-1-yl)-8-bromoxanthine

A mixture of 40.00 g of 3-methyl-8-bromoxanthine, 36 ml of diisopropylethylamine and 23.00 g of 1-bromo-2-butyne in 500 ml of N,N-dimethylformamide is stirred at room temperature for three hours. 1 ml of 1-bromo-2-butyne is then added again and the mixture is stirred at room temperature for a further hour until the reaction is complete. For work-up, the reaction mixture is diluted with 400 ml of water. The resulting precipitate is filtered off with suction, washed with water, cold methanol and diethyl ether and dried.

Yield: 41.60 g (86% of theory) Mass spectrum (ESI$^+$): m/z=297, 299 [M+H]$^+$

EXAMPLE III

2-Chloromethyl-4-methylquinazoline

Prepared by treatment of 2.95 g of 2-chloromethyl-4-methylquinazoline 3-oxide with 6 ml of phosphorus trichloride in 150 ml of chloroform under reflux.

Yield: 1.75 g (57% of theory) $R_f$: 0.81 (silica gel, methylene chloride/methanol=95:5) Mass spectrum (ESI$^+$): m/z=193, 195 [M+H]$^+$

EXAMPLE IV 1-(Bromomethyl)-4-cyanoisoquinoline

Prepared by treatment of 2.40 g of 1-methyl-4-cyanoisoquinoline with 2.60 g of N-bromosuccinimide in the presence of 100 mg of azobisisobutyronitrile in carbon tetrachloride under reflux.

Yield: 704 mg (20% of theory) $R_f$: 0.58 (silica gel, methylene chloride) Mass spectrum (ESI$^+$): m/z=247, 249 [M+H]$^+$ The following compounds are obtained analogously to Example IV:

(1) 3-(Bromomethyl)-1-cyanoisoquinoline $R_f$: 0.62 (silica gel, methylene chloride)

(2) 2-(Bromomethyl)-[1,5]-naphthyridine

Mass spectrum (ESI$^+$): m/z=223, 225 [M+H]$^+$ $R_f$: 0.65 (silica gel, methylene chloride)

Preparation of the final compounds:

EXAMPLE 1

1-[(4-Methylquinazolin-2-yl)methyl]-3-methyl-7-(2-butyn-1-yl)-8-(piperazin-1-yl)-xanthine A mixture of 300 mg of 1-[(4-methylquinazolin-2-yl)methyl]-3-methyl-7-(2-butyn-1-yl)-8-bromoxanthine and 290 mg of piperazine in 5 ml of N,N-dimethylformamide is heated at 200° C. for 5 min in a microwave oven. After cooling to room temperature, the reaction mixture is treated with water and saturated sodium chloride solution and extracted with ethyl acetate. The organic phase is washed with saturated sodium chloride solution, dried over magnesium sulphate and concentrated. The solid flask residue is triturated with diethyl ether, filtered off with suction and dried at 45° C. in a circulating air drying oven.

Yield: 200 mg (66% of theory) Melting point: 213-215° C. Mass spectrum (ESI$^+$): m/z=459 [M+H]$^+$ The following compounds are obtained analogously to Example 1:

(1) 1-[(3-Methylisoquinolin-1-yl)methyl]-3-methyl-7-(2-butyn-1-yl)-8-(piperazin-1-yl)-xanthine $R_f$: 0.50 (reversed phase TLC ready-to-use plates (E. Merck), acetonitrile/water/trifluoroacetic acid=50:50:1) Mass spectrum (ESI$^+$): m/z=458 [M+H]$^+$ (2) 1-[(3-Methylisoquinolin-1-yl)methyl]-3-methyl-7-(2-butyn-1-yl)-8-([1,4]diazepan-1-yl)xanthine Melting point: 129-13 1° C. Mass spectrum (ESI$^+$): m/z=472 [M+H]$^+$ (3) 1-[(4-Methylquinazolin-2-yl)methyl]-3-methyl-7-(2-butyn-1-yl)-8-([1,4]diazepan-1-yl)xanthine Melting point: 188-190° C. Mass spectrum (ESI$^+$): m/z=473 [M+H]$^+$ (4) 1-[(Phenanthridin-6-yl)methyl]-3-methyl-7-(2-butyn-1-yl)-8-(piperazin-1-yl)xanthine $R_f$: 0.50 (reversed phase TLC ready-to-use plate (E. Merck), acetonitrile/water/trifluoroacetic acid=50:50:1) Mass spectrum (ESI$^+$): m/z=494 [M+H]$^+$ (5) 1-[(Phenanthridin-6-yl)methyl]-3-methyl-7-(2-butyn-1-yl)-8-([1,4]diazepan-1-yl)-xanthine Melting point: 223-225° C. Mass spectrum (ESI$^+$): m/z=508 [M+H]$^+$ (6) 1-[(4-Phenylquinazolin-2-yl)methyl]-3-methyl-7-(2-butyn-1-yl)-8-(piperazin-1-yl)-xanthine $R_f$: 0.49 (silica gel, methylene chloride/methanol/conc. aqueous ammonia=90:10:1) Mass spectrum (ESI$^+$): m/z=521 [M+H]$^+$ (7) 1-[(2,3-Dimethylquinoxalin-6-yl)methyl]-3-methyl-7-(2-butyn-1-yl)-8-(piperazin-1-yl)xanthine $R_f$: 0.38 (silica gel, methylene chloride/methanol/conc. aqueous ammonia=90:10:1) Mass spectrum (ESI$^+$): m/z=473 [M+H]$^+$ (8) 1-[(4-Cyanoisoquinolin-1-yl)methyl]-3-methyl-7-(2-butyn-1-yl)-8-(piperazin-1-yl)-xanthine $R_f$: 0.39 (silica gel, methylene chloride/methanol/conc. aqueous ammonia=90: 10:1) Mass spectrum (ESI$^+$): m/z=469 [M+H]$^+$ (9) 1-[(1-Cyanoisoquinolin-3-yl)methyl]-3-methyl-7-(2-butyn-1-yl)-8-(piperazin-1-yl)-xanthine $R_f$: 0.34 (silica gel, methylene chloride/methanol/conc. aqueous ammonia=90:10:1) Mass spectrum (ESI$^+$): m/z=469 [M+H]$^+$

(10) 1-[([1,5]-Naphthyridin-2-yl)methyl]-3-methyl-7-(2-butyn-1-yl)-8-(piperazin-1-yl)-xanthine $R_f$: 0.46 (silica gel, methylene chloride/methanol/conc. aqueous ammonia=90:10:1) Mass spectrum (ESI$^+$): m/z=445 [M+H]$^+$ The following compounds can also be obtained analogously to the above examples and other processes known from the literature:

1-[(4-Methylquinazolin-2-yl)methyl]-3-phenyl-7-(2-butyn-1-yl)-8-(piperazin-1-yl)-xanthine 1-[(4-Methylquinazolin-2-yl)methyl]-3-cyclopropyl-7-(2-butyn-1-yl)-8-(piperazin-1-yl)-xanthine 1-[(4-Cyanonaphthalen-1-yl)methyl]-3-methyl-7-(2-butyn-1-yl)-8-(piperazin-1-yl)-xanthine 1-[(4-Methoxynaphthalen-1-yl)methyl]-3-methyl-7-(2-butyn-1-yl)-8-(piperazin-1-yl)-xanthine 1-[(4-Fluoronaphthalen-1-yl)methyl]-3-methyl-7-(2-butyn-1-yl)-8-(piperazin-1-yl)-xanthine 1-[(4-Dimethylaminoquinazolin-2-yl)methyl]-3-methyl-7-(2-butyn-1-yl)-8-(piperazin-1-yl)xanthine 1-{[4-(Morpholin-4-yl)quinazolin-2-yl]methyl}-3-methyl-7-(2-butyn-1-yl)-8-(piperazin-1-yl)xanthine 1-[([1,5]Naphthyridin-2-yl)methyl]-3-methyl-7-(2-butyn-1-yl)-8-([1,4]diazepan-1-yl)-xanthine 1-[(2-Methylquinolin-4-yl)methyl]-3-methyl-7-(2-butyn-1-yl)-8-(piperazin-1-yl)xanthine 1-[(7-Fluoroquinolin-2-yl)methyl]-3-methyl-7-(2-butyn-1-yl)-8-(piperazin-1-yl)-xanthine 1-[(4-Phenylpyrimidin-2-yl)methyl]-3-methyl-7-(2-butyn-1-yl)-8-(piperazin-1-yl)-xanthine 1-[(1-Cyanoisoquinolin-3-yl)methyl]-3-methyl-7-(2-butyn-1-yl)-8-([1,4]diazepan-1-yl)-xanthine 1-[(Quinazolin-6-yl)methyl]-3-methyl-7-(2-butyn-1-yl)-8-(piperazin-1-yl)xanthine 1-[(Isoquinolin-1-yl)methyl]-3-methyl-7-(2-butyn-1-yl)-8-(piperazin-1-yl)xanthine 1-[(Quinolin-4-yl)methyl]-3-methyl-7-(2-butyn-1-yl)-8-(piperazin-1-yl)xanthine 1-[(4-Cyanoquinazolin-2-yl)methyl]-3-methyl-7-(2-butyn-1-yl)-8-(piperazin-1-yl)-xanthine 1-[(3-Cyanoquinolin-2-yl)methyl]-3-methyl-7-(2-butyn-1-yl)-8-(piperazin-1-yl)xanthine 1-[(1,4-Dicyanonaphthalen-2-yl)methyl]-3-methyl-7-(2-butyn-1-yl)-8-(piperazin-1-yl)-xanthine

EXAMPLE 2

Coated Tablets Containing 75 mg of Active Substance

| 1 coated tablet core contains: | |
|---|---|
| Active substance | 75.0 mg |
| Calcium phosphate | 93.0 mg |
| Maize starch | 35.5 mg |
| Polyvinylpyrrolidone | 10.0 mg |
| Hydroxypropylmethylcellulose | 15.0 mg |
| Magnesium stearate | 1.5 mg |
| | 230.0 mg |

Preparation:

The active substance is mixed with calcium phosphate, maize starch, polyvinylpyrrolidone, hydroxypropylmethylcellulose and half the stated amount of magnesium stearate. Pressings having a diameter of about 13 mm are prepared on a tabletting machine; these are grated through a sieve having a mesh width of 1.5 mm on a suitable machine and blended with the remaining amount of magnesium stearate. These granules are pressed on a tabletting machine to give tablets having the desired shape.

Core weight: 230 mg

Die: 9 mm, convex

The coated tablet cores thus prepared are coated with a film which consists essentially of hydroxypropylmethylcellulose. The finished film-coated tablets are glazed with beeswax. Coated tablet weight: 245 mg.

EXAMPLE 3

Tablets Containing 100 mg of Active Substance

Composition:

| 1 tablet contains: | |
|---|---|
| Active substance | 100.0 mg |
| Lactose | 80.0 mg |
| Maize starch | 34.0 mg |
| Polyvinylpyrrolidone | 4.0 mg |
| Magnesium stearate | 2.0 mg |
| | 220.0 mg |

Preparation Process:

Active compound, lactose and starch are mixed and uniformly moistened with an aqueous solution of the polyvinylpyrrolidone. After sieving the moist mass (2.0 mm mesh width) and drying in a tray drying oven at 50° C., the mixture is sieved again (1.5 mm mesh width) and the lubricant is admixed. The press-ready mixture is compressed to give tablets.

Tablet weight: 220 mg

Diameter: 10 mm, biplanar with a facet on both sides and a breaking notch on one side.

EXAMPLE 4

Tablets Containing 150 mg of Active Substance

Composition:

| 1 tablet contains: | |
|---|---|
| Active substance | 150.0 mg |
| Lactose, powdered | 89.0 mg |
| Maize starch | 40.0 mg |
| Colloidal silicic acid | 10.0 mg |
| Polyvinylpyrrolidone | 10.0 mg |
| Magnesium stearate | 1.0 mg |
| | 300.0 mg |

Preparation:

The active substance mixed with lactose, maize starch and silicic acid is moistened with a 20% strength aqueous polyvinylpyrrolidone solution and pounded through a sieve having a mesh width of 1.5 mm.

The granules dried at 45° C. are again grated through the same sieve and mixed with the stated amount of magnesium stearate. Tablets are pressed from the mixture.

Tablet weight: 300 mg

Die: 10 mm, flat

EXAMPLE 5

Hard Gelatine Capsules Containing 150 mg of Active Substance

| 1 capsule contains: | | |
|---|---|---|
| Active compound | | 150.0 mg |
| Maize starch, dried | about | 180.0 mg |
| Lactose, powdered | about | 87.0 mg |
| Magnesium stearate | | 3.0 mg |
| | about | 420.0 mg |

Preparation:

The active compound is blended with the excipients, passed through a sieve of mesh width 0.75 mm and homogeneously mixed in a suitable apparatus.

The final mixture is filled into hard gelatine capsules of size 1.

Capsule filling: about 320 mg

Capsule shell: hard gelatine capsule size 1.

EXAMPLE 6

Suppositories Containing 150 mg of Active Substance

1 Suppository Contains:

| 1 suppository contains: | |
|---|---|
| Active compound | 150.0 mg |
| Polyethylene glycol 1500 | 550.0 mg |
| Polyethylene glycol 6000 | 460.0 mg |
| Polyoxyethylenesorbitan monostearate | 840.0 mg |
| | 2000.0 mg |

Preparation:

After melting the suppository mass, the active compound is homogeneously dispersed therein and the melt is poured into precooled moulds.

EXAMPLE 7

Suspension Containing 50 mg of Active Substance 100 ml of Suspension Contain:

| 100 ml of suspension contain: | |
|---|---|
| Active compound | 1.00 g |
| Carboxymethylcellulose Na salt | 0.10 g |
| Methyl p-hydroxybenzoate | 0.05 g |
| Propyl p-hydroxybenzoate | 0.01 g |
| Sucrose | 10.00 g |
| Glycerol | 5.00 g |
| Sorbitol solution, 70% strength | 20.00 g |
| Flavouring | 0.30 g |
| water, dist. | to 100 ml |

Preparation:

Dist. water is heated to 70° C. Methyl and propyl p-hydroxybenzoate and also glycerol and carboxymethylcellulose sodium salt are dissolved therein with stirring. The mixture is cooled to room temperature and the active compound is added and homogeneously dispersed with stirring. After adding and dissolving the sugar, the sorbitol solution and the flavouring, the suspension is evacuated with stirring for deaeration. 5 ml of suspension contain 50 mg of active compound.

EXAMPLE 8

Ampoules Containing 10 mg of Active Substance

Composition:

| Composition: | |
|---|---|
| Active compound | 10.0 mg |
| 0.01N hydrochloric acid | q. s. |
| Water, double-distilled | to 2.0 ml |

Preparation:

The active substance is dissolved in the required amount of 0.01 N HCl, rendered isotonic using sodium chloride, sterile-filtered and filled into 2 ml ampoules.

EXAMPLE 9

Ampoules Containing 50 mg of Active Substance

Composition:

| Composition: | |
|---|---|
| Active compound | 50.0 mg |
| 0.01N hydrochloric acid | q. s. |
| Water, double-distilled | to 10.0 ml |

Preparation:

The active substance is dissolved in the required amount of 0.01 N HCl, rendered isotonic using sodium chloride, sterile-filtered and filled into 10 ml ampoules.

What is claimed is:

1. A compound of formula

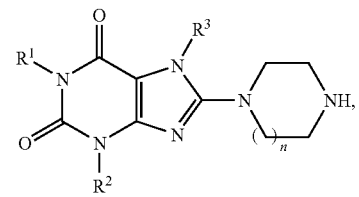

(I)

wherein $R^1$ is (a) a heteroaryl-$C_{1-3}$-alkyl group,
wherein heteroaryl is selected from the group consisting of phenylpyrimidinyl, quinolinyl, isoquinolinyl, quinazolinyl, quinoxalinyl, naphthyridinyl and phenanthridinyl which may be optionally substituted by $R^{10}$, $R^{11}$ and $R^{12}$,
where $R^{10}$ is selected from hydrogen, fluorine, chlorine, bromine, methyl, difluoromethyl, trifluoromethyl, phenyl, cyano, methoxy, difluoromethoxy, trifluoromethoxy, amino, methylamino, dimethylamino, pyrrolidin-1-yl, piperidin-1-yl or morpholin-4-yl group;
$R^{11}$ is selected from hydrogen, methyl, methoxy or cyano; and
$R^{12}$ is hydrogen or methyl, or (b) a naphthyl-$C_{1-3}$-alkyl group, which may be substituted by $R^{13}$ and $R^{14}$,
where $R^{13}$ is selected from hydrogen, fluorine, chlorine, bromine methyl, difluoromethyl, trifluoromethyl, cyano, methoxy, difluoromethoxy or trifluoromethoxy; and
$R^{14}$ is selected from hydrogen, methyl, methoxy or cyano;

$R^2$ is selected from methyl, ethyl, propyl, isopropyl, cyclopropyl or phenyl;

$R^3$ is selected from 2-butyn-1-yl, 1-buten-1-yl, 2-buten-1-yl or 3-methyl-2-buten-1-yl and n is 1 or 2;

or a tautomer, enantiomer, diastereomer, mixture, prodrug or salt thereof.

2. The compound of formula I according to claim 1, wherein
R¹ is
(a) a heteroarylmethyl group,
wherein heteroaryl is selected from the group consisting of phenylpyrimidinyl, quinolinyl, isoquinolinyl, quinazolinyl, quinoxalinyl, naphthyridinyl and phenanthridinyl, which may be optionally substituted by $R^{10}$, $R^{11}$ and $R^{12}$,
where $R^{10}$ is selected from hydrogen, methyl, difluoromethyl, trifluoromethyl, phenyl, cyano, methoxy, difluoromethoxy, trifluoromethoxy, amino, methylamino, dimethylamino, pyrrolidin-1-yl, piperidin-1-yl or morpholin-4-yl;
$R^{11}$ is selected from hydrogen, methyl or cyano; and
$R^{12}$ is selected from hydrogen or methyl,
or
(b) a naphthylmethyl group, which may optionally be substituted by $R^{13}$ and $R^{14}$,
where $R^{13}$ is selected from hydrogen, fluorine, chlorine, bromine, methyl, difluoromethyl,
trifluoromethyl, cyano, methoxy, difluoromethoxy or trifluoromethoxy; and
$R^{14}$ is selected from hydrogen, methyl or cyano;
$R^2$ is selected from methyl, ethyl, propyl, isopropyl, cyclopropyl or phenyl;
$R^3$ is selected from 2-butyn-1-yl, 1-buten-1-yl, 2-buten-1-yl or 3-methyl-2-buten-1-yl;
and
n is 1 or 2;
or a tautomer, mixture or their salt thereof.

3. The compound of formula I according to claim 1, wherein
R¹ is
(a) a heteroarylmethyl group,
where heteroaryl is selected from a group consisting of phenylpyrimidinyl, quinolinyl, isoquinolinyl, quinazolinyl, quinoxalinyl, naphthyridinyl or phenanthridinyl, which may optionally substituted by $R^{10}$, $R^{11}$ and $R^{12}$,
where $R^{10}$ is selected from hydrogen, methyl, phenyl, cyano, methoxy, amino, methylamino, dimethylamino, pyrrolidin-1-yl, piperidin-1-yl or morpholin-4-yl;
$R^{11}$ is selected from hydrogen, methyl or cyano; and
$R^{12}$ is selected from hydrogen or methyl,
or
(b) a naphthylmethyl group, which optionally may be substituted by $R^{13}$ and $R^{14}$,
where $R^{13}$ is selected from hydrogen, fluorine, methyl, cyano or methoxy; and
$R^{14}$ is selected from hydrogen, methyl or cyano;
$R^2$ is methyl;
$R^3$ is 2-butyn-1-yl;
and
n is 1 or 2;
or a tautomer, mixture or salt thereof.

4. The compound of formula I according to claim 1, wherein
R¹ is methyl, which may be substituted by a fluoronaphthyl, methoxynaphthyl, cyanonaphthyl, dicyanonaphthyl, phenylpyrimidinyl, quinolinyl, fluoroquinolinyl, methylquinolinyl, cyanoquinolinyl, isoquinolinyl, methylisoquinolinyl, cyanoisoquinolinyl, quinazolinyl, methylquinazolinyl, phenylquinazolinyl, (dimethylamino)-quinazolinyl, (morpholin-4-yl)quinazolinyl, quinoxalinyl, methylquinoxalinyl, dimethylquinoxalinyl, trimethylquinoxalinyl, phenylquinoxalinyl or naphthyridinyl;
$R^2$ is methyl;
$R^3$ is 2-butyn-1-yl;
and
n is 1 or 2;
or a tautomer, mixture or salt thereof.

5. The compound of formula I according to claim 1, wherein
R¹ is methyl, which may be substituted by a cyanoquinolinyl, methylisoquinolinyl, cyanoisoquinolinyl, quinazolinyl, methylquinazolinyl, phenylquinazolinyl, dimethylquinoxalinyl or naphthyridinyl group;
$R^2$ is methyl;
$R^3$ is 2-butyn-1-yl;
and
n is 1 or 2;
or a tautomer, mixture or salt thereof.

6. The compound of formula I according to any one of claims 1 to 5, wherein
$R^1$, $R^2$ and $R^3$ are as defined;
and
n is 1;
or a tautomer, mixture or salt thereof.

7. The compound of formula I according to any one of claims 1 to 5, wherein
$R^1$, $R^2$ and $R^3$ are as defined;
and
n is 2;
or a tautomer or salt thereof.

8. The compound of formula I according to claim 1 is selected from:
(a) 1-[(4-Methylquinazolin-2-yl)methyl]-3-methyl-7-(2-butyn-1-yl)-8-(piperazin-1-yl)-xanthine
(b) 1-[(4-Phenylquinazolin-2-yl)methyl]-3-methyl-7-(2-butyn-1-yl)-8-(piperazin-1-yl)-xanthine
(c) 1-[([1,5]-Naphthyridin-2-yl)methyl]-3-methyl-7-(2-butyn-1-yl)-8-(piperazin-1-yl)-xanthine or a tautomer or salt thereof.

9. A physiologically tolerable salt of a compound according to one of claims 1-5 or 8 with at least one inorganic or organic acid.

10. A medicament comprising a compound according to claim 1 or a physiologically tolerable salt thereof in addition to one or more inert vehicles and/or diluents.

11. A method of treating at least one of diabetes mellitus type II and adiposity comprising administering to a patient in need thereof an effective amount of a compound according to claim 1 or a physiologically tolerable salt thereof.

12. A process for the preparation of the compounds of the general formula I according to claim 1, wherein
a) a compound of the formula

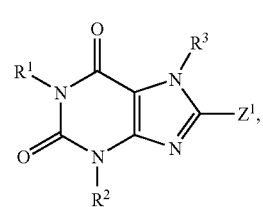

(II)

in which
R[1] to R[3] are as defined in claim 1, and
Z[1] is a leaving group selected from a chlorine or bromine atom, or a methanesulfonyl or methanesulfonyloxy group,
is reacted with piperazine or [1,4]diazepane or their salts, wherein, optionally, reactive groups optionally present in formula (II) are protected with a protective group during the reaction and the protective group is cleaved after the reaction, or b) a compound of the formula

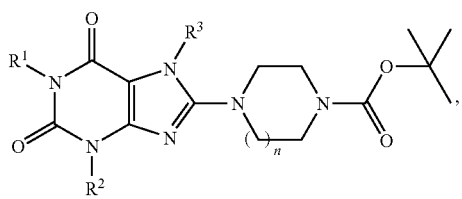
(III)

wherein R[1], R[2] and R[3] are defined as mentioned in claim 1, is deprotected by removing the tert-butyloxycarbonyl group.

13. The process according to claim 12 further comprising separating a compound thus obtained into its enantiomers and/or diastereomers.

14. The process according to claim 12 further comprising converting a compound thus obtained into at least one salt thereof with an inorganic or organic acid.

15. The process according to claim 13 further comprising converting a compound thus obtained into at least one salt thereof with an inorganic or organic acid.

16. A process for the preparation of the compounds of the formula I according to claim 1, wherein a) a compound of the formula

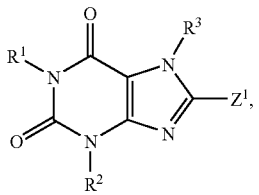
(II)

in which
R[1] to R[3] are defined in claim 1, and
Z[1] is a leaving group,
is reacted with piperazine or [1,4]diazepane or their salts, wherein, optionally, reactive groups optionally present in formula (II) are protected with a protective group during the reaction and the protective group is cleaved after the reaction, or b) a compound of the formula

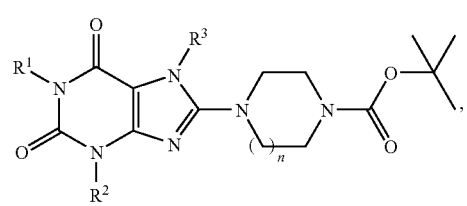
(III)

wherein R[1], R[2] and R[3] are as defined in claim 1, is deprotected by removing the tert-butyloxycarbonyl group.

* * * * *